(12) United States Patent
Piechaczek et al.

(10) Patent No.: US 7,538,213 B2
(45) Date of Patent: May 26, 2009

(54) METHODS FOR PREPARATION OF OLANZAPINE POLYMORPHIC FORM I

(75) Inventors: Janina Piechaczek, Warszawa (PL); Magdalena Glice, Warszawa (PL); Urszula Fraczek, Marki (PL); Jadwiga Serafin, Warszawa (PL); Wieslaw Szelejewski, Warszawa (PL); Krzysztof Soltysiak, Warszawa (PL)

(73) Assignee: Institut Farmaceutyczny, Warszawa (PL)

( * ) Notice: Subject to any disclaimer, the term of this patent is extended or adjusted under 35 U.S.C. 154(b) by 584 days.

(21) Appl. No.: 10/514,520

(22) PCT Filed: May 16, 2003

(86) PCT No.: PCT/PL03/00044

§ 371 (c)(1),
(2), (4) Date: Jun. 20, 2005

(87) PCT Pub. No.: WO03/097650

PCT Pub. Date: Nov. 27, 2003

(65) Prior Publication Data

US 2005/0239772 A1    Oct. 27, 2005

(30) Foreign Application Priority Data

May 17, 2002    (PL) .................................... 353989

(51) Int. Cl.
*C07D 495/04*    (2006.01)

(52) U.S. Cl. ...................................... 540/557
(58) Field of Classification Search .................. 540/557
See application file for complete search history.

(56) References Cited

U.S. PATENT DOCUMENTS

| 5,229,382 A | 7/1993 | Chakrabarti et al. |
| 5,637,584 A | 6/1997 | Larsen |
| 6,348,458 B1 | 2/2002 | Hamied et al. |

FOREIGN PATENT DOCUMENTS

| EP | 0 454 436 B1 | 9/1995 |
| EP | 0 733 635 B1 | 8/2001 |
| WO | WO 96/38151 | 12/1996 |
| WO | WO 00/18408 | 4/2000 |
| WO | WO 02/18390 A1 | 3/2002 |
| WO | WO 03/097650 A1 | 11/2003 |

OTHER PUBLICATIONS

PCT International Search Report for International of Aug. 22, 2003 for PCT Patent Application No. PCT/PL03/00044, filed May 16, 2003, International Publication No. WO 03/897650 A1, published Nov. 27, 2003.
Reply to a Written Opinion of Jan. 20th, 2004.

*Primary Examiner*—Brenda L Coleman
(74) *Attorney, Agent, or Firm*—Husch Blackwell Sanders LLP Welsh & Katz

(57) ABSTRACT

The invention relates to the methods for preparation of olanzapine polymorphic Form I. The invention also provides new mixed solvates of olanzapine, which are valuable intermediates used in the preparation of pure olanzapine polymorphic Form I.

13 Claims, 5 Drawing Sheets

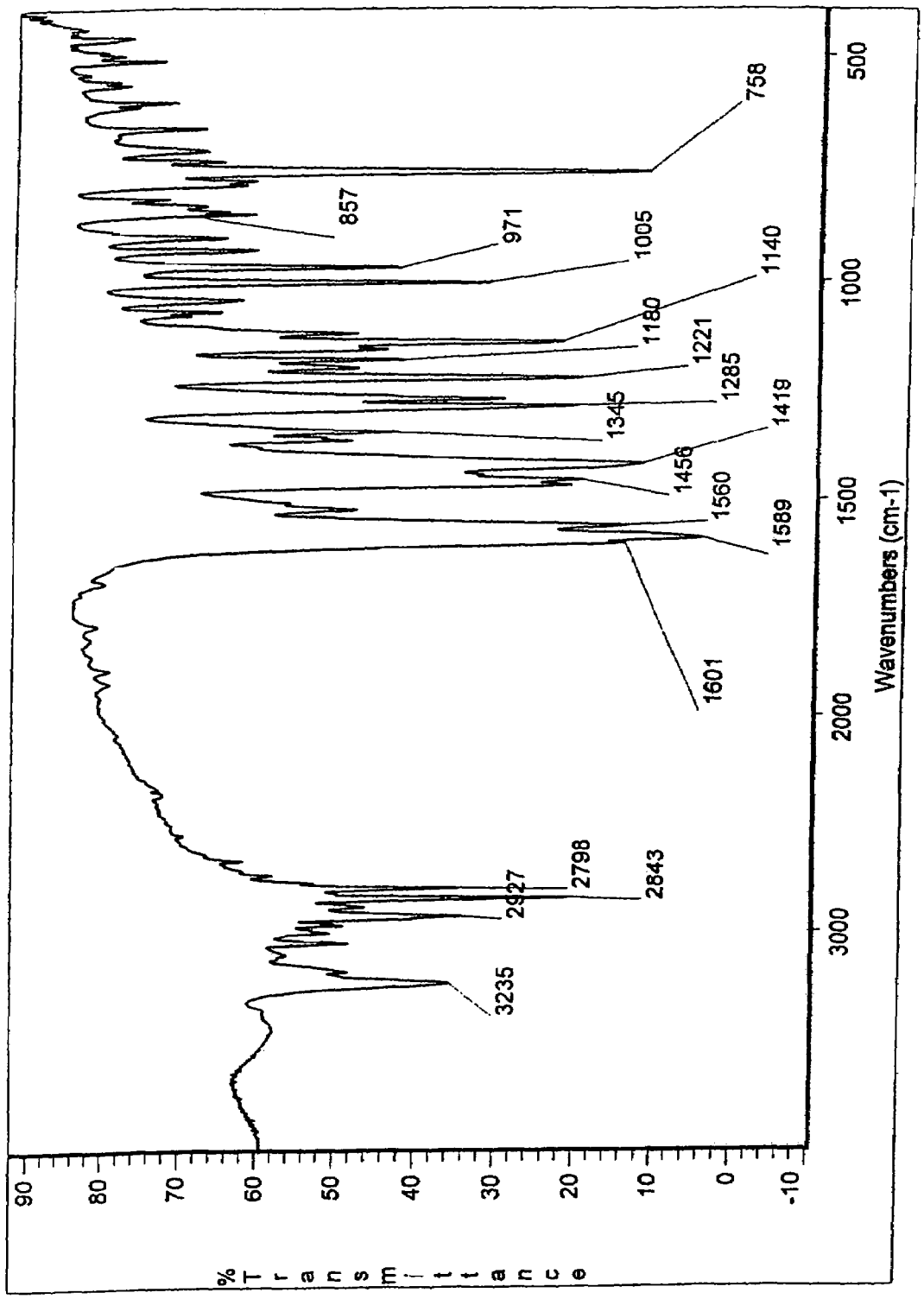
Fig.1. Infrared spectrum of olanzapine polymorphic Form I

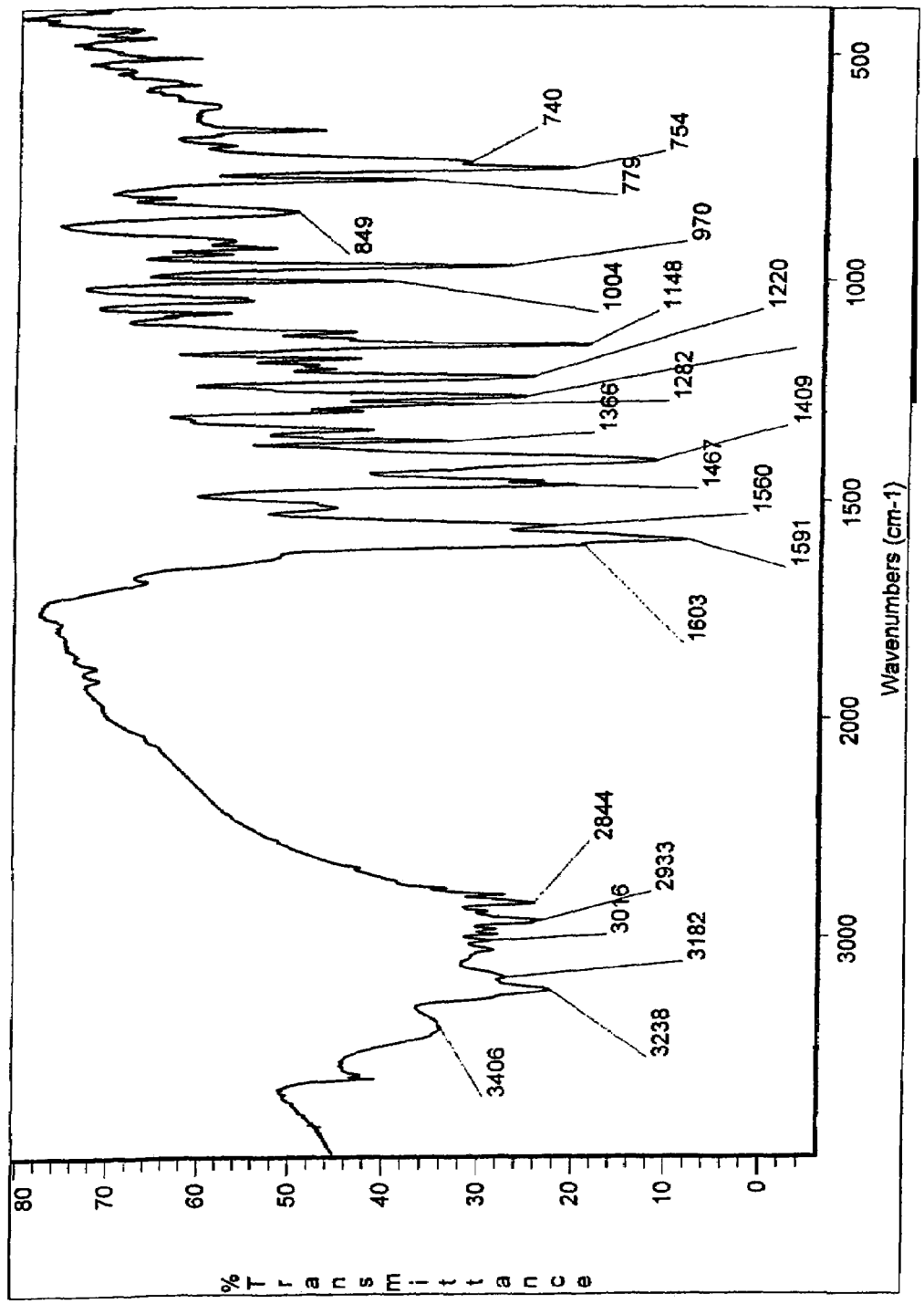
Fig.2. Infrared spectrum of the solvate (1) of olanzapine with methylene chloride and water

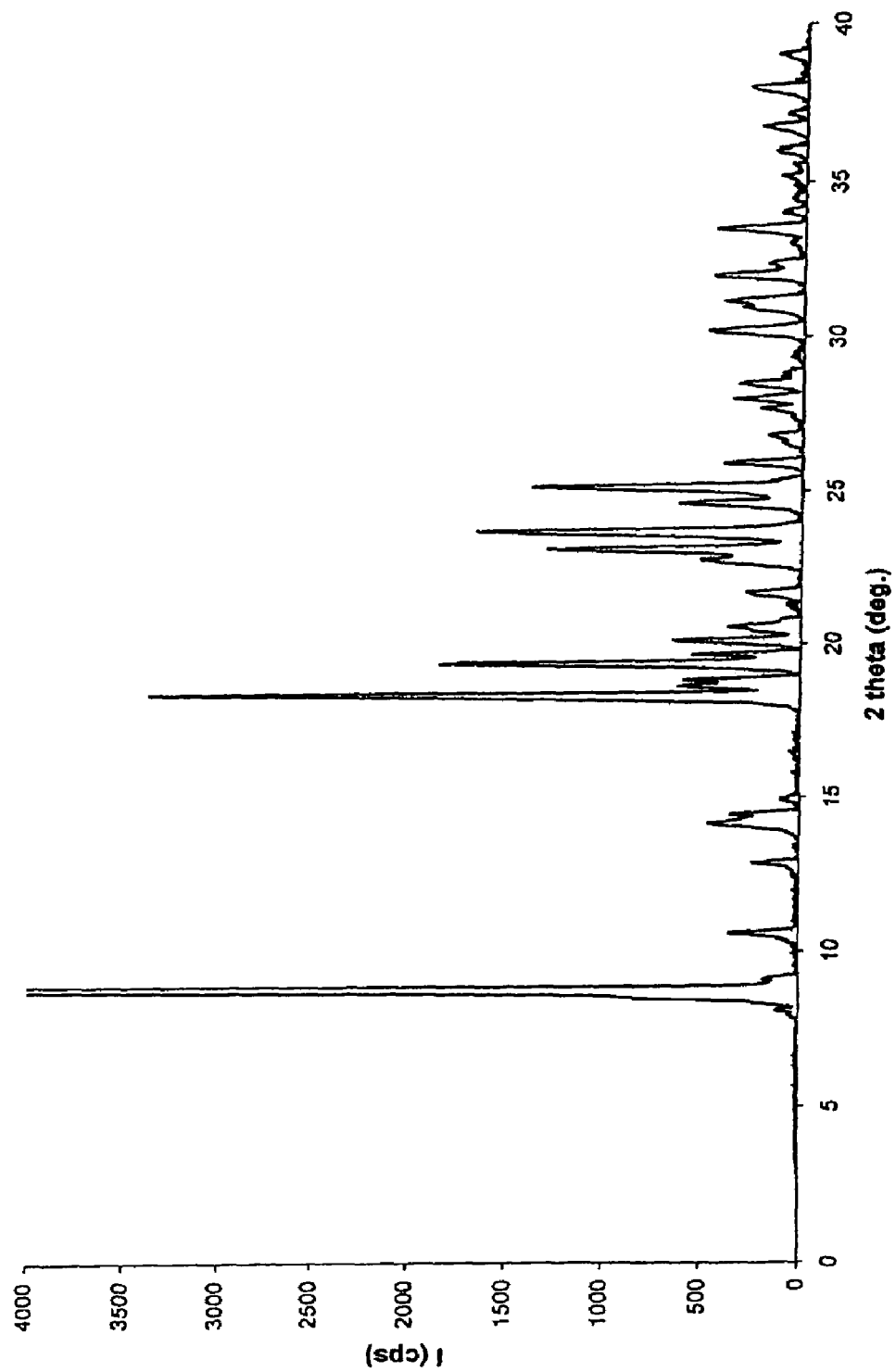
Fig.3. X-ray powder diffractogram of the solvate (1) of olanzapine with methylene chloride and water

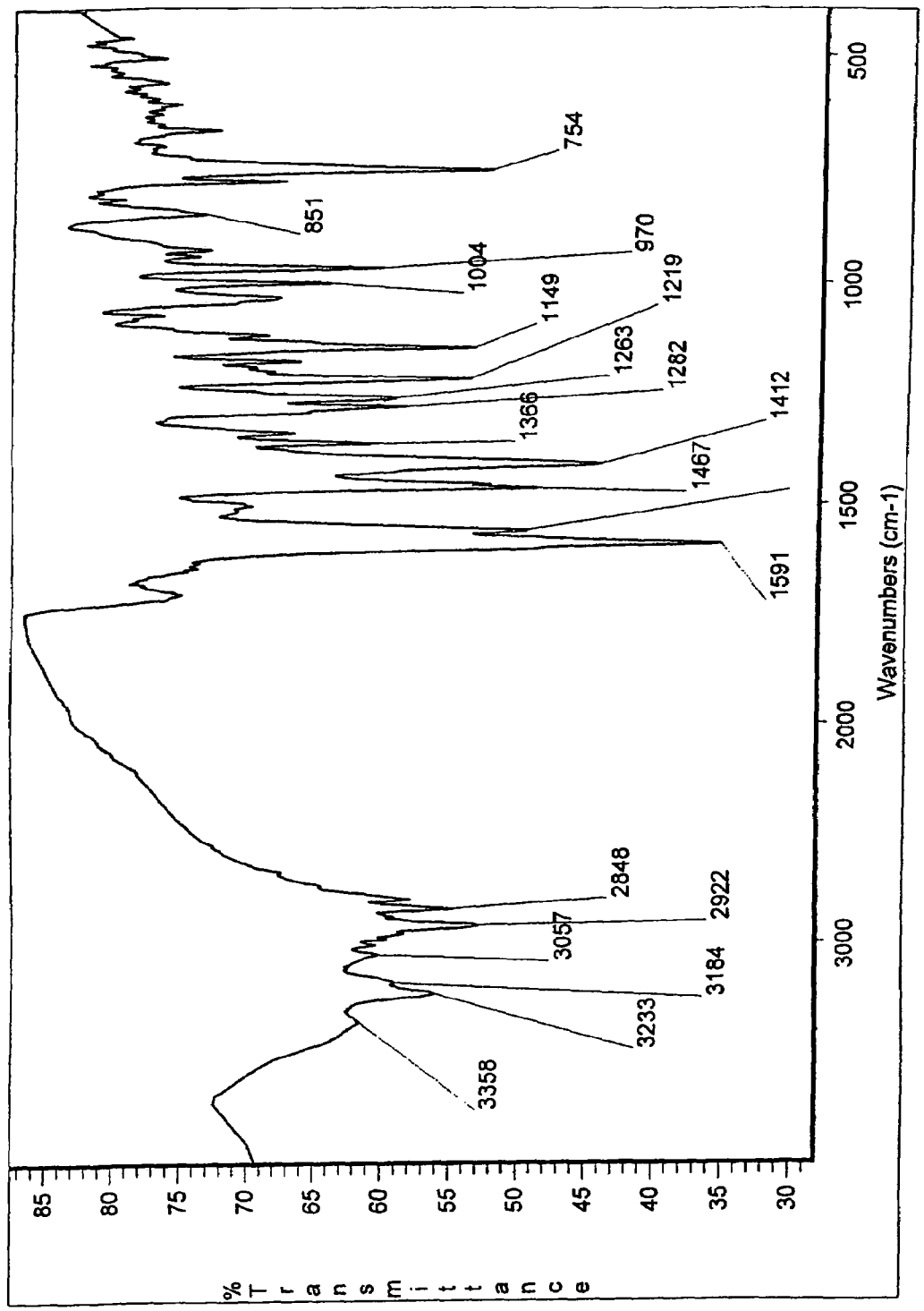
Fig.4. Infrared spectrum of the solvate (2) of olanzapine with dimethylsulfoxide and water

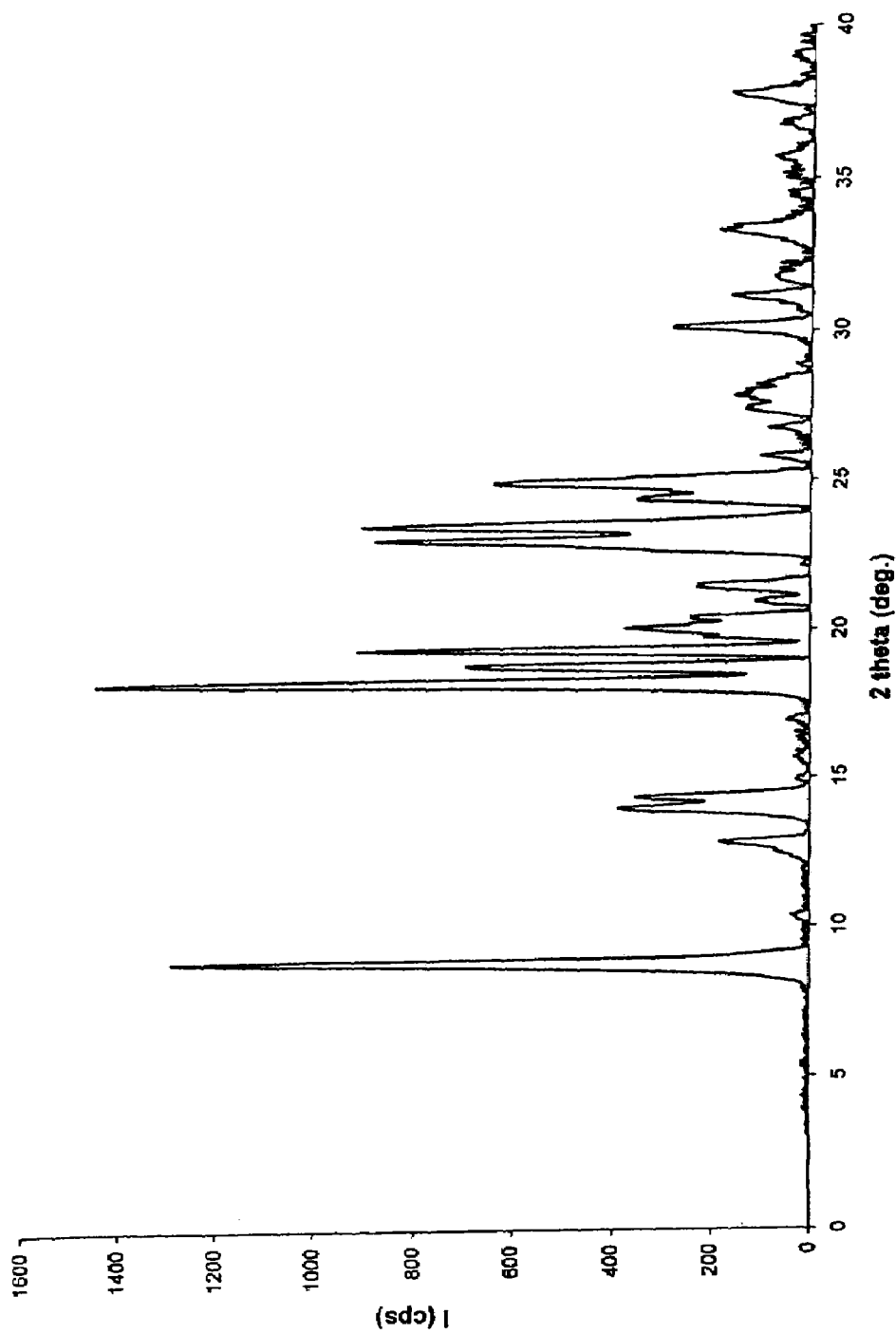
Fig.5. X-ray powder diffractogram of the solvate (2) of olanzapine with dimethylsulfoxide and water

METHODS FOR PREPARATION OF OLANZAPINE POLYMORPHIC FORM I

CROSS REFERENCES TO RELATED APPLICATIONS

This application is a national phase application based upon priority International PCT Patent Application No. PCT/PL03/00044, filed May 16, 2003, International Publication No. WO 03/097650 A1, published Nov. 27, 2003, which is based upon priority Polish Application No. P-353989 filed May 17, 2002.

BACKGROUND OF THE INVENTION

1. Field of the Invention

The invention relates to the methods for preparation of olanzapine polymorphic Form I. The invention also relates to the new mixed solvates of olanzapine which are valuable intermediates used in the preparation of pure olanzapine polymorphic Form I.

2. Background of the Invention

Olanzapine, 2-methyl-4-(4-methyl-1-piperazinyl)-10H-thieno-[2,3b][1,5]benzodiazepine is a potent antipsychotic agent. Olanzapine as a free base or its hydrochloride salt is an active ingredient of pharmaceutical preparations used in the treatment of disorders of the central nervous system.

Olanzapine was described for the first time in the European Patent Application EP 0454436 A1. One of the disclosed methods for preparation of olanzapine (Example 1, Point 4) is based on condensation of 4-amine-2-methyl-10H-thieno[2,3-b][1,5]benzodiazepine with N-methylpiperazine carried out in dimethylsulfoxide and toluene. At the final stage of the reaction, water is added and a crude product thus isolated is crystallized from acetonitrile.

In the second method (Example 2, Point 3), a crude product is obtained by cyclization of 1-{[2-amine-aniline)-5-metyhlthiophen-3-yl]carbonyl}-4-methyl-piperazine carried out in N-methylpiperazine and anisole, isolated by treating with ammonia, isopropanol and ethyl acetate and finaly purified. Purification is performed by column chromatography with the use of Florisil eluted with ethyl acetate and the product is further crystallized from acetonitrile.

Both methods disclosed in EP 0454436 A1 lead to obtain olanzapine in a pure crystalline form which is characterized by a specific melting point, NMR spectra ($^1$H and $^{13}$C) and mass spectrum.

The European Patent Application EP 0733635 A1 discloses that olanzapine can exist in two different polymorphic crystalline forms which differ from each other by their stability, physical properties and spectral characteristics. Polymorph as prepared by the procedures according to EP 0454436 A1 comprising the crystallization from acetonitrile has been denominated Form I and it has been described to be metastable and not suitable for commercial use in pharmaceutical formulations such as tablets due to its color, which changes over time on exposure to air.

In EP 0733635 A1, a more thermodynamically stable second polymorph of olanzapine is claimed. Accordingly, olanzapine polymorphic Form II is obtained by suspending crude olanzapine in ethyl acetate in anhydrous conditions and crystallization from this solution. The occurrence of olanzapine in two different polymorphic forms has been confirmed by X-ray powder diffraction patterns which are characterized by different interplanar spacings (d) and relative intensities ($I/I_0$).

Thus, the practical process for the preparation of olanzapine described in EP 0454436 A1 and in the subsequent documents of the prior art, for example in WO 96/38151 and WO 02/18390, comprises the condensation of a molar excess of N-methylpiperazine with 4-amine-2-methyl-10H-thieno-[2,3-b][1,5]benzodiazepine hydrochloride in the mixture of dimethylsulfoxide and toluene. When the reaction is completed, excess of water and/or another hydroxylic solvent is added to remove unreacted substrates and to isolate a crude product. After cooling, the crude product is separated in the form of solvate. Depending on the method used for crystallization of the intermediate solvate, polymorphic form I or II of olanzapine is obtained.

However, the methods of the prior art are rather difficult to reproduce and often do not lead to obtaining the anticipated olanzapine polymorphic form.

For example, following the procedure of Preparation 1 of EP 0828494 (WO 96/38151), the obtaining of polymorphic Form II is declared. However, the X-ray powder diffraction pattern of the product matches with that of olanzapine Form I as claimed in EP 0733635 A1.

On the other hand, in WO 96/38151, preperation methods are given for a polymorph defined as olanzapine Form I, consisting in the crystallization of crude product from acetone (Preparation 6), butyl acetate (Preparation 7), t-butanol (Preparation 8) and in transformation of Form I carried out in toluene.

It is fair to assume that olanzapine Form II of WO 96/38151 is the polymorph denominated Form I in EP 0733635.

This conclusion has been evidenced in a laboratory practice, where the use of any solvent, such as acetonitrile, tetrahydrofuran, acetone, toluene or ethyl acetate, for crystallization of crude olanzapine always resulted in crystalline Form II, identified by X-ray powder diffraction patterns described in EP 0733635. The only one solvent enabling to obtain olanzapine polymorphic Form I by crystallization of crude olanzapine or its crystalline Form II, is methylene chloride.

The use of intermediate solvate of olanzapine with methylene chloride for obtaining anhydrous Form I of olanzapine is disclosed in U.S. Pat. No. 5,637,584. The solvate of olanzapine with methylene chloride is prepared by suspending technical grade olanzapine in methylene chloride, heating and stirring the mixture at 30° C., chilling the mixture to 5° C. and isolating the product.

According to U.S. Pat. No. 5,637,584, technical grade olanzapine may be defined as 2-methyl-4-(4-methyl-1-piperazinyl)10H-thieno[2,3-b][1,5]benzodiazepine when no specific solvate or polymorph is named. Typically, the technical grade olanzapine contains less than 5% undesired related substances and may be a mixed polymorph.

But, in a laboratory practice it is observed that olanzapine obtained by the methods of prior art, comprising the reaction of a molar excess of N-methylpiperazine with 4-amine-2-methyl-10H-thieno[2,3-b][1,5]benzodiazepine in organic solvent, eg. dimethylsulfoxide and toluene, and subsequent addition of water and/or hydroxylic solvent, usually contains much more than 5% of impurities; in some experiments the level of impurities exceeds 10-15%. As a consequence more than single, mostly at least triple, crystallization from different solvents is required to remove these impurities to obtain olanzapine of pharmaceutical grade. Optionally one additional crystallization is needed to transform olanzapine into a desired polymorphic form.

As concerns the method for preparing a technical grade olanzapine, U.S. Pat. No. 5,637,584 especially refers to U.S. Pat. No. 5,229,382. Moreover, according to U.S. Pat. No.

5,637,584, olanzapine prepared by a method described in U.S. Pat. No. 5,229,382 is a crude product exhibiting a colour, which colour is difficult to be removed with typically used methods (eg. with the aid of charcoal). This undesired coloration is a result of impurities content.

In Preparation 4 of WO 96/38151, for obtaining a technical grade olanzapine, crude olanzapine is recrystallized from toluene. After drying in vacuo at 50° C., such obtained technical grade olanzapine requires further recrystallization from ethyl acetate/toluene/methanol to give a methanol solvate, which is converted, upon drying, to an anhydrous technical grade olanzapine.

Thus, a technical grade olanzapine obtained as above, still contains undesired related substances and may be a mixture of polymorphs, so it needs further processing to transform it into crystalline pure polymorphic Form I. The method for transforming olanzapine obtained in Preparation 4 of WO 96/38151 into olanzapine Form I comprises suspending crude olanzapine in methylene chloride, stirring the mixture at ambient temperature, chilling the filtrate and evaporating ¾ of solvent. Then, into the thick paste prechilled methylene chloride is mixed, the solid product is isolated and dried at first on the air and then at 50° C. in a vaccum oven. Product obtained is olanzapine Form I and $CH_2Cl_2$ solvate. Only re-drying this product at 50° C. gives pure polymorphic Form I of olanzapine.

Independently, the use of methylene chloride for crystallization of olanzapine in polymorphic Form I via intermediate monohydrate-1 and dihydrate-2 forms of olanzapine has been described in an International Patent Publication WO 02/18390. Intermediate hydrates are formed by adding water to the reaction mixture formed after completion of the reaction of 4-amine-2-methyl-10H-thieno[2,3-b][1,5]benzodiazepine hydrochloride with N-methyl-piperazine in the mixture of dimethylsulfoxide and toluene, then by cooling and isolating the precipitate. The degree of hydration of the resulting intermediates depends on time of drying of the samples. Neither monohydrate-1 nor dihydrate-2 contains methylene chloride or dimethylsulfoxide. These intermediates are transformed into olanzapine polymorphic Form I by heating to reflux in methylene chloride. The process according to WO 02/18390 is a laborious one, as it needs isolating the intermediate hydrates and controlling the parameters of their drying, on the contrary the product may be non-homogenous.

Teaching of the above-mentioned documents as well as the failure of the attempts to reproduce the prior art methods for preparation of olanzapine polymorphic Form I free of other polymorphs and pseudopolymorphs, have proned us to find an efficient method for isolation and purification of olanzapine Form I, which method would be suitable for technical scale processes.

BRIEF SUMMARY OF THE INVENTION

This was accomplished according to the present invention, by developing the methods for the preparation of pure olanzapine polymorphic Form I, in which the crude olanzapine is recovered from the reaction mixture and purified by using methylene chloride as the same, single solvent.

The invention further provides new mixed solvates of olanzapine which are valuable intermediates used in the preparation of pure olanzapine polymorphic Form I.

One aspect of the invention is the solvate (1) of olanzapine with methylene chloride and water.

Another aspect of the invention is the solvate (2) of olanzapine with dimethylsulfoxide and water.

Another aspect of the invention is pure olanzapine free of solvates and impurities, prepared by one of the methods according to the invention.

A more detailed description of the invention is provided in the following description and appended claims taken in conjunction with the accompanying drawings.

BRIEF DESCRIPTION OF THE DRAWINGS

FIG. 1 represents the infrared spectrum of olanzapine polymorphic Form I.

FIG. 2 represents the infrared spectrum of solvate (1) of olanzapine with methylene chloride and water.

FIG. 3 represents the X-ray powder diffractogram of solvate (1) of olanzapine with methylene chloride and water.

FIG. 4 represents the infrared spectrum of solvate (2) of olanzapine with dimethylsulfoxide and water.

FIG. 5 represents the X-ray powder diffractogram of solvate (2) of olanzapine with dimethylsulfoxide and water.

DETAILED DESCRIPTION OF THE INVENTION

The following is a detailed description and explanation of the preferred embodiments and best modes for embodying the invention along with some examples thereof.

As used herein, the term "pure olanzapine polymorphic Form I" refers to olanzapine polymorphic Form I associated with not more than 5%, preferably not more than 2%, and the most preferably not more than 1% of the other polymorphic form, as may be detected by typical spectroscopic methods. Furthermore, the term "pure olanzapine polymorphic Form I" relates to a chemical compound which preferably contains not more than about 2%, more preferably not more than 1%, and the most preferably not more than 0.5% of undesired chemical impurities, such as unreacted substrates, residual solvents or water.

The polymorphic form of olanzapine prepared according to the methods of the invention as well as the structure of its solvates, have been determined by infrared spectroscopy (IR) in KBr and X-ray powder diffraction.

Particularly, the difference between polymorphic Form I and II of olanzapine could be demonstrated by infrared spectroscopy. The Fourier Transform Infrared (FTIR) spectra were recorded in KBr pellet with Nicolet Impact system 400 spectrometer, with a resolution of 4 $cm^{-1}$, from 4000 $cm^{-1}$ to 400 $cm^{-1}$.

The comparison of characteristic bands of olanzapine polymorphs I and II in terms of wavelengths and intensity shows that they differ significantly, particularly in the range of N-H vibrations.

The greatest differences in the spectra are within the following ranges: 3320-3000, 1680-1490, 980-950, 920-860, 780-730 $cm^{-1}$, and particularly in the range 920-860 $cm^{-1}$. These differences result from hydrogen bonds of various strength in polymorphs of olanzapine. The example of IR spectrum of olanzapine polymorphic Form I is presented in FIG. 1.

X-Ray powder diffraction patterns of olanzapine polymorphic forms have been determined with a Rigaku MINI FLEX diffractometer in the range of 3-40° in 2θ (deg, for CuKα, λ=1,542 Å; scanning rate 0.5 deg/min, scanning step 0.03 deg) and presented as the interplanar spacings d versus the relative intensity $I/I_0$ (expressed as a percentage of the most intense reflection).

The significant powder diffraction reflections of olanzapine polymorphic forms I and II show significant differences.

Polymorph I of olanzapine is considered the one characterized by the following interplanar spacings d and the relative intensity $I/I_0$:

| d ($m^{-10}$) | $I/I_0$ |
|---|---|
| 9.9497 | 56 |
| 8.5644 | 16 |
| 8.2304 | 9 |
| 6.8779 | 10 |
| 4.9731 | 11 |
| 4.8333 | 100 |
| 4.7511 | 41 |
| 4.6283 | 26 |
| 4.5391 | 35 |
| 4.4622 | 8 |
| 4.2387 | 27 |
| 4.0919 | 45 |
| 3.8209 | 15 |
| 3.7478 | 39 |
| 3.7017 | 56 |
| 3.5842 | 9 |
| 3.5090 | 18 |
| 3.3482 | 12 |
| 3.2406 | 8 |
| 3.1121 | 13 |
| 2.9511 | 6 |
| 2.8219 | 8 |
| 2.7575 | 8 |
| 2.5975 | 11 |
| 2.4648 | 11 |
| 2.3816 | 6 |
| 2.3328 | 12 |

The present invention relates to the process of isolation and purification of crude olanzapine prepared by any method known from the art, especially of olanzapine obtained in condensation of molar excess of N-methylpiperazine with 4-amine-2-methyl-10H-thieno[2,3-b][1,5]benzodiazepine hydrochloride, carried out in an organic solvent. The preferred organic solvent is dimethylsulfoxide.

In the first embodiment of the invention, the crude olanzapine is extracted from the reaction mixture by diluting it with an excess volume of a mixture of methylene chloride and water.

In that preferred embodiment of the invention, methylene chloride and water is used in a proportion 2:1 (v/v).

Then, the separated organic layer is washed with water and evaporated, and the residue is cooled to 0-5° C. The precipitated solvate (1) is filtered off and washed, with maceration, with methylene chloride.

The structure of the precipitated product has been analyzed by X-ray powder diffraction and infrared spectroscopy in KBr pellets. The composition of the solvate (1) has been further analyzed by gas chromatography (GC) for substrates content, by thin layer chromatography (TLC) for impurities presence and by Carl-Fischer method for water content.

The X-ray powder diffractogram of solvate (1) is characterized by the following interplanar spacings d and relative intensities $I/I_0$:

| d ($m^{-10}$) | $I/I_0$ |
|---|---|
| 10.0857 | 100 |
| 8.3466 | 4 |
| 6.8726 | 3 |
| 6.2625 | 5 |
| 6.1329 | 4 |
| 4.8359 | 32 |

-continued

| d ($m^{-10}$) | $I/I_0$ |
|---|---|
| 4.7061 | 6 |
| 4.5832 | 18 |
| 4.5071 | 5 |
| 4.4139 | 6 |
| 4.3182 | 4 |
| 4.0938 | 3 |
| 3.9071 | 5 |
| 3.8470 | 13 |
| 3.7556 | 16 |
| 3.6157 | 6 |
| 3.5434 | 13 |
| 3.4345 | 4 |
| 3.3286 | 2 |
| 3.2257 | 2 |
| 3.1850 | 4 |
| 3.1324 | 4 |
| 2.9587 | 5 |
| 2.8914 | 3 |
| 2.8696 | 4 |
| 2.7962 | 5 |
| 2.7633 | 2 |
| 2.6742 | 5 |
| 2.4454 | 2 |
| 2.3671 | 3 |

The IR spectrum of solvate (1) of olanzapine (Nicolet FTIR spectrometer Impact 400, KBr pellet, resolution 4 $cm^{-1}$) is characterized by the bands observed at the following frequencies ($cm^{-1}$): 3406, 3238, 2933, 2844, 1591, 1467, 1409, 1366, 1282, 1265, 1220, 1148, 1004, 970, 849, 779, 754, 740. The IR spectrum of solvate (1) differs significantly from the IR spectrum of polymorphic Forms I and II of olanzapine.

The analytical methods confirmed that the precipitated solid is a solvate (1) of crude olanzapine with methylene chloride and water, containing less than 5% of reaction impurities.

The solvate (1) of crude olanzapine consists of 4 molecules of olanzapine, 1 molecule of methylene chloride and 8 molecules of water.

The solvate (1), according to the method of the invention, is dried in vacuo and crystallized from methylene chloride to give pure polymorphic Form I of olanzapine. Single crystallization of solvate (1) from methylene chloride is sufficient to obtain a pharmaceutically pure olanzapine containing not more than 0.5% of impurities.

According to the second embodiment of the invention, the crude olanzapine is isolated from the reaction mixture by diluting it with water, after precipitation of the solvate (2) of olanzapine containing not more than 5% of reaction impurities. The solvate (2), as identified with the use of above-mentioned methods, is a solvate of crude olanzapine with dimethylsulfoxide and water.

The solvate (2) consists of 4 molecules of olanzapine, 1 molecule of dimethylsulfoxide and 2 molecules of water.

The X-ray diffractogram (Rigaku MINI FLEX diffractometer, according to procedure described above) of the solvate shows the following interplanar spacings d and relative intensities $I/I_0$:

| d ($m^{-10}$) | $I/I_0$ |
|---|---|
| 10.0172 | 90 |
| 6.9047 | 13 |
| 6.3565 | 26 |
| 6.1841 | 25 |
| 4.8755 | 100 |

-continued

| d (m⁻¹⁰) | I/I₀ |
|---|---|
| 4.7285 | 48 |
| 4.5974 | 64 |
| 4.5003 | 14 |
| 4.4270 | 26 |
| 4.3496 | 17 |
| 4.2387 | 8 |
| 4.1333 | 16 |
| 3.8718 | 60 |
| 3.7888 | 63 |
| 3.6508 | 24 |
| 3.5771 | 45 |
| 3.4502 | 8 |
| 3.2604 | 9 |
| 3.1884 | 9 |
| 2.9673 | 20 |
| 2.8696 | 12 |
| 2.6883 | 13 |
| 2.3798 | 12 |

In the IR spectrum of solvate (2) of olanzapine (Nicolet FTIR spectrometer Impact 400, KBr pellet, resolution 4 cm$^{-1}$) the bands were observed at the following frequencies (cm$^{-1}$): 3358, 3233, 2922, 2848, 1591, 1467, 1412, 1366, 1282, 1263, 1219, 1149, 1004, 970, 851, 754. The spectrum differs insignificantly from the IR spectrum of solvate (1). However, it differs significantly from IR spectra of polymorphs I and II of olanzapine.

The solvate (2), according to the second embodiment of the method of the present invention, is further crystallized twice from methylene chloride to give a pure olanzapine polymorphic Form I.

The methods of isolation and purification of crude olanzapine according to the present invention allow avoiding undesired coloration of olanzapine polymorphic Form I. Such coloration occurs in the methods known from the art. Even single crystallization of the intermediate solvate is sufficient for the purification of the crude product, so to yield olanzapine polymorphic Form I of impurities content less than 0.5%. The use of the single and the same organic solvent, ie. methylene chloride, for isolation of crude olanzapine from the reaction mixture as well as for its purification is advantageous due to the strict quality requirements, which should be met by the pharmaceutical grade product.

Olanzapine polymorphic Form I obtained by the method according to the invention is characterized by high stability under typical storing conditions at room temperature as well as in the conditions of the accelerated ageing test. After 2 years of storing the samples of olanzapine polymorphic Form I at 25° C. and 60% RH, no differences were observed in the range or the intensity of bands in IR spectrum and X-ray powder diffractogram.

The following examples are provided for the purposes of illustration merely, and are not to be constructed as limiting the scope of the claimed invention.

EXAMPLES

Example 1

The reaction mixture of 4-amine-2-methyl-10H-thieno[2,3-b][1,5]benzodiazepine hydrochloride (25 g) and N-methylpiperazine (72 g) in dimethylsulfoxide (63 g) was refluxed at 115-120° C. for 8-10 hours. After completing the reaction (determined by HPLC), the mixture was cooled to ambient temperature and methylene chloride (300 g, 400 mL) and water (200 mL) were added. The mixture was stirred for 15 minutes, and then left for further 20 minutes when the spontaneous separation of layers was observed. The layers were separated, and the organic layer was washed with water (85 mL) and dried under vacuum at 35° C. After evaporating of the solvents, the residue (170 g) was cooled to 0° C. and maintained at this temperature for 5 h. The precipitated solid was centrifuged, washed, with maceration, with cold methylene chloride (5 mL), to give 20 g of wet solid identified as solvate (1) of olanzapine-CH$_2$Cl$_2$-water. The solid was dissolved in hot methylene chloride, the solution was evaporated in vacuo and cooled, to give the product identified by X-ray powder diffraction and IR spectroscopy as olanzapine polymorphic Form I, m.p. 195° C.; total impurities (HPLC) <0.3%.

Example 2

A mixture of 4-aminomethyl-10H-thieno[2,3-b][1,5]benzodiazepine hydrochloride (335.8 g) (82%, as calculated for the free base), N-methylpiperazine (960 g) and dimethylsulfoxide (880 g) was heated at 120° C. under nitrogen atmosphere for 8-10 h. The reaction was carried out until the spot of the substrate disappeared on TLC. After completing the reaction, the reaction mixture was cooled, water was added (3.6 L) and stirring was continued for 3 h. The mixture was then filtered; the precipitate was washed with water to give 500 g of wet solid product, which was then dried at 50° C. The obtained solid was identified as solvate (2) of olanzapine-DMSO-water and was crystallized from methylene chloride (600 mL) with charcoal. After evaporation of the solvent (about ⅔ volume), the solution was cooled to 0° C., the solid was isolated by filtration and the wet product was crystallized again from the same amount of methylene chloride, to yield 225 g of pure olanzapine polymorphic Form I, m.p. 195° C.; total impurities (BPLC).

Although embodiments and examples of the invention have been shown and described, it is to be understood that various modifications, substitutions, and rearrangements of compounds, elements, components, features, and process steps, as well as other methods of preparing the compounds of the invention, can be made by those skilled in the art without departing from the novel spirit and scope of the invention.

What is claimed is:

1. A method for preparation of pure olanzapine polymorphic Form I, characterized in that the crude olanzapine prepared in condensation of molar excess of N-methylpiperazine with 4-amine-2-methyl-10H-thieno [2,3-b][1,5]benzodiazepine hydrochloride carried out in dimethylsulfoxide, is recovered from the reaction mixture and purified by using methylene chloride as the same, single solvent.

2. The method according to claim 1, characterized in that the crude olanzapine is extracted from the reaction mixture by diluting it with the excess volume of the mixture of methylene chloride and water, then the separated organic layer is washed with water and evaporated, the residue is cooled to 0-5° C., the precipitated solvate is filtered off, washed, with maceration, with methylene chloride, and crystallized from methylene chloride.

3. The method according to claim 2, characterized in that a crude olanzapine is extracted with the mixture of methylene chloride and water in a proportion of 2:1 (v/v).

4. A solvate of crude olanzapine with methylene chloride and water in a proportion 4 molecules of olanzapine: 1 molecule of methylene chloride: 8 molecules of water.

5. The solvate according to claim 4, characterized by the following interplanar spacings d and relative intensities $I/I_0$ in an X-ray diffractogram:

| d (m$^{-10}$) | $I/I_0$ |
|---|---|
| 10.0857 | 100 |
| 8.3466 | 4 |
| 6.8726 | 3 |
| 6.2625 | 5 |
| 6.1329 | 4 |
| 4.8359 | 32 |
| 4.7061 | 6 |
| 4.5832 | 18 |
| 4.5071 | 5 |
| 4.4139 | 6 |
| 4.3182 | 4 |
| 4.0938 | 3 |
| 3.9071 | 5 |
| 3.8470 | 13 |
| 3.7556 | 16 |
| 3.6157 | 6 |
| 3.5434 | 13 |
| 3.4345 | 4 |
| 3.3286 | 2 |
| 3.2257 | 2 |
| 3.1850 | 4 |
| 3.1324 | 4 |
| 2.9587 | 5 |
| 2.8914 | 3 |
| 2.8696 | 4 |
| 2.7962 | 5 |
| 2.7633 | 2 |
| 2.6742 | 5 |
| 2.4454 | 2 |
| 2.3671 | 3. |

6. The solvate according to claim 5, characterized by bands in a IR spectrum recorded from KBr pellet at the following wavenumbers (cm$^{-1}$): 3406, 3238, 2933, 2844, 1591, 1467, 1409, 1366, 1282, 1265, 1220, 1148, 1004, 970, 849, 779, 754, 740.

7. The method for preparation of olanzapine polymorphic Form I according to claim 1, characterized in that the crude olanzapine is isolated from the reaction mixture by diluting the reaction mixture with a volume excess of water, in form of solvate (2), and the wet solvate is crystallized twice from methylene chloride.

8. A solvate of olanzapine with dimethylsulfoxide and water in proportion of 4 molecules of olanzapine: 1 molecule of dimethylsulfoxide: 2 molecules of water.

9. The solvate according to claim 8, characterized by the following interplanar distances d and relative intensities $I/I_0$ in a X-ray diffractogram:

| d (m$^{-10}$) | $I/I_0$ |
|---|---|
| 10.0172 | 90 |
| 6.9047 | 13 |
| 6.3565 | 26 |
| 6.1841 | 25 |
| 4.8755 | 100 |
| 4.7285 | 48 |
| 4.5974 | 64 |
| 4.5003 | 14 |
| 4.4270 | 26 |
| 4.3496 | 17 |
| 4.2387 | 8 |
| 4.1333 | 16 |
| 3.8718 | 60 |
| 3.7888 | 63 |
| 3.6508 | 24 |
| 3.5771 | 45 |
| 3.4502 | 8 |
| 3.2604 | 9 |
| 3.1884 | 9 |
| 2.9673 | 20 |
| 2.8696 | 12 |
| 2.6883 | 13 |
| 2.3798 | 12. |

10. A solvate according to claim 8 characterized by the absorption in IR spectrum recorded form KBr pellet at the following wavenumbers (cm$^{-1}$) 3358, 233, 2922, 2848, 1591, 1467, 1412, 1366, 1282, 1263, 1219, 1149, 1004, 970, 851, 754.

11. The crystalline pure olanzapine prepared by the method according to claim 2.

12. The crystalline pure olanzapine prepared by the methods according to claim 7.

13. The solvate according to claim 5, characterized by bands in a IR spectrum recorded from KBr pellet at the following frequencies (cm$^{-1}$): 3406, 3238, 2933, 2844, 1591, 1467, 1409, 1366, 1282, 1265, 1220, 1148, 1004, 970, 849, 779, 754, 740.

* * * * *